(12) United States Patent
Rapp

(10) Patent No.: US 6,310,267 B1
(45) Date of Patent: Oct. 30, 2001

(54) FLEXIBLE WOUND COVERING BASED ON FIBRIN AND PROCESS FOR ITS PRODUCTION

(75) Inventor: Mirna Rapp, Marburg (DE)

(73) Assignee: Aventis Behring GmbH, Marburg (DE)

(*) Notice: Subject to any disclaimer, the term of this patent is extended or adjusted under 35 U.S.C. 154(b) by 0 days.

(21) Appl. No.: 09/434,104

(22) Filed: Nov. 5, 1999

(30) Foreign Application Priority Data

Nov. 6, 1998 (DE) .............................. 198 51 334

(51) Int. Cl.[7] .................................................. A61F 13/00
(52) U.S. Cl. ................... 602/41; 602/42; 602/43; 602/44; 602/45; 602/46; 602/47; 602/48
(58) Field of Search .......................... 602/41–50

(56) References Cited

U.S. PATENT DOCUMENTS

| 2,492,458 | 12/1949 | Bering . |
| 4,407,787 | 10/1983 | Stemberger . |
| 4,427,651 | 1/1984 | Stroetmann . |
| 5,407,671 | 4/1995 | Heimburger et al. . |

FOREIGN PATENT DOCUMENTS

| 30 37 513 A1 | 4/1982 | (DE) . |
| 32 14 337 A1 | 10/1983 | (DE) . |
| 0 068 149 A2 | 1/1983 | (EP) . |
| 0 090 997 A2 | 10/1983 | (EP) . |
| 0 485 210 A2 | 5/1992 | (EP) . |

OTHER PUBLICATIONS

European Search Report dated Feb. 15, 2000.
English language Derwent of European Abstract EP 0090 997.

*Primary Examiner*—Mickey Yu
*Assistant Examiner*—Lalita M. Hamilton
(74) *Attorney, Agent, or Firm*—Finnegan, Henderson, Farabow, Garrett and Dunner, L.L.P.

(57) ABSTRACT

A biodegradable, flexible wound covering based on fibrin and a process for its preparation are described, in which a fibrinogen solution is subjected to a single-stage or multi-stage dialysis, then a flexible fibrin web is formed by action of an aqueous thrombin solution on the fibrinogen solution and this is subsequently subjected to freeze-drying.

18 Claims, No Drawings

FLEXIBLE WOUND COVERING BASED ON FIBRIN AND PROCESS FOR ITS PRODUCTION

The invention relates to a flexible, biodegradable fibrin web for wound healing, and its production. Web materials of this type can be employed for hemostasis on internal and external wounds and also as carrier materials for biological factors.

It is known that surgical interventions on internal organs are accompanied by problems of wound closure, caused by the strong blood flow and softness of the tissue. A frequently used method for the closure of internal wounds is electro-coagulation of the blood vessels, which in most cases leads to postoperative adhesions which are painful for the patient. Moreover, it is only of limited suitability for the closure of posttraumatic organ ruptures. A good alternative is fibrin adhesive, with which the wound is closed by means of preceding reaction of a number of endogenous, human clotting factors. The clot in this case formed on the wound is distinguished by a high compatibility and rapid hemostasis. Less advantageous is the longer preparation time preceding the application of the fibrin adhesive and the somewhat involved application, especially in minimally invasive surgery, where a special applicator is needed for the endoscope. Therefore attempts have also already been made to develop a biodegradable wound covering based on fibrin, which is available ready-for-use and can be applied to the wound without special preparation. A web material of this type is disclosed in European Patent Application 0 068 149, which is directed at a fibrinogen-containing dry preparation which has a foam or web structure achieved by freeze-drying and, in addition to thrombin in at least catalytically active amounts, consists essentially of approximately 10 to 95% by weight of fibrin and approximately 5 to 90% by weight of fibrinogen. In the production of a web-like wound covering, fibrin is in this case first produced in a fibrinogen- and thrombin-containing aqueous solution and the resulting reaction mixture is deep-frozen and lyophilized. This material is especially intended as a wound care material, as a filling material for bone cavities and/or as a carrier material for further active compounds. A serious disadvantage of this wound covering consists, however, in the fact that what is concerned here is a rigid and fragile web, which maintains its rigidity even after contact with water or blood. As a result, the application possibilities of a fibrin web of this type are extremely restricted. Moreover, an absorbable, multilayer sheet material which contains at least one thrombin-free and at least one fibrinogen-free component layer, which in each case have a glycoprotein matrix, is disclosed in German Patent 32 14 337. As a result of the spatial separation of thrombin and fibrinogen, in this case the formation of a fibrin web is prevented.

There has therefore been no lack of attempts to develop more suitable wound coverings from other biological materials. Webs are found on the market which consist of a biological material such as collagen, which is mainly obtained from animal connective tissue from cattle, from horses or from pigs. Thus EP-A 0 485 210, for example, has proposed a fibrin-containing collagen membrane.

Materials of this type, however, require virus inactivation and particular safety measures in order to avoid potential transmission of the BSE infective agents. Moreover, cases of patients with hypersensitivity reactions to bovine collagen have been reported in the literature. Therefore it has already been thought of making available collagen webs of human material, for example of collagen which is obtained from the placenta. Although this could admittedly have a better biocompatibility, it is likewise affected by the problem of virus safety. The idea has therefore also already been expressed of employing recombinant or transgenic human collagen for the production of wound coverings, but collagen of this type, even in the present state of development, is still not competitive for reasons of cost. Finally, in U.S. Pat. No. 2,492,458 a fibrin foam is disclosed which can be introduced permanently into a wound for hemostasis.

Finally, it has also already been thought of employing synthetically prepared, biodegradable materials, such as polyhydroxycarboxylic acids or polyamino acids, for the production of degradable wound coverings.

Although these materials admittedly offer a more economical alternative to recombinant collagen, their use is restricted, as they are not very suitable for hemostasis in heavily bleeding and soft tissues. Moreover, they are more poorly compatible, as during their use products which can cause inflammatory reactions in the body are formed by degradation processes.

The object was therefore to develop a biodegradable wound covering which avoids the known disadvantages of the wound coverings customary until now. This object is achieved according to the invention by means of a biodegradable wound covering based on fibrin, which as a result of particular process steps used in its production has a high flexibility and is therefore outstandingly suitable as a web for the covering and closure of bleeding wounds.

It has now been found that a biodegradable, flexible wound covering based on fibrin, in which the wound covering is a fibrin web or contains a fibrin web which is largely or completely free of dialyzable constituents, meets these demands. In this case, the fibrin web is preferably firmly combined with a biodegradable carrier material. A fibrin web is particularly suitable which contains 10–80% by weight of glycerol per fibrin unit.

A wound covering of this type based on fibrin can be produced according to the invention by a process in which a fibrinogen solution is subjected to a single-stage or multistage dialysis, then a flexible fibrin web is formed by action of an aqueous thrombin solution on the fibrinogen solution and this is subsequently subjected to freeze-drying.

As a result of the single-stage or multistage dialysis of the fibrinogen solution, its composition is crucially changed and the concentrations of salts and amino acids customarily contained in it are considerably reduced. It is assumed that this is the crucial prerequisite for the production of a flexible fibrin web. The dialysis of the fibrinogen solution can be carried out in various ways. With a single-stage solution, the fibrinogen solution is treated in a dialysis bath which simultaneously contains an organic complexing agent and physiologically compatible inorganic salts. The single-stage dialysis, however, can also be carried out using a dialysis bath which exclusively contains organic complexing agents. Then, after completion of the dialysis, the physiologically compatible inorganic salt, as a rule NaCl, is added to the fibrinogen solution in an amount of 0.05 to 0.5 percent by weight.

Organic complexing agents added in the dialysis are especially alkali metal salts of ethylenediaminetetraacetic acid, of oxalic acid or of citric acid. The concentration of the organic complexing agent in the dialysis bath is in general 1 to 20 mM, preferably 1 to 5 mM.

However, it is also possible to carry out the dialysis in two stages. In this case, in the first dialysis step the fibrinogen solution is dialyzed with an aqueous solution of one of the abovementioned complex salts and subsequently in a second dialysis bath the dialysis with an NaCl solution or the solution of another physiologically tolerable inorganic salt is carried out.

The fibrinogen thus freed of dialyzable concomitants, which can also still contain the addition of factor XIII customary in fibrin adhesive preparations, is an outstandingly suitable starting substance for the production of a flexible fibrin web. This is produced by mixing the dialyzed fibrinogen solution with an aqueous solution of thrombin and calcium chloride. In this process, the water-soluble calcium salt is present, as a rule, in an amount from 0.5 to 40 mM. In general, the fibrinogen is employed for the production of the fibrin web in an amount from 10 to 25 g/l and the thrombin is employed in an amount of up to 100 I.U./ml. The production of the fibrin web takes place at a temperature between 0 and 37° C.

For production of the fibrin web, the thrombin/calcium chloride solution can be admixed to the fibrinogen solution, but it is much more advantageous to spray the thrombin/calcium chloride solution onto the fibrinogen solution introduced into a flat dish. For production of a fibrin web which is a number of meters wide, the thrombin/calcium chloride solution is sprayed onto the fibrinogen solution contained in an appropriately wide trough of liquid from spray heads arranged in rows which move over the fibrinogen solution in a uniform manner. After a reaction time sufficient for the formation of the fibrin web, it is subsequently subjected to drying, preferably freeze-drying. The freeze-drying is preferably carried out in the following manner:

The fibrin web is frozen at −28° C. for two hours and then dried in vacuo at the same temperature for twelve hours. Two drying steps at −10° C. and +20° C. for 16 and 8 hours in each case then follow, likewise in vacuo.

A particularly advantageous wound covering according to the invention based on fibrin can be prepared if the fibrin web is combined with a biodegradable carrier material. A suitable carrier material for this is especially natural or chemically modified collagen, keratin, gelatin, carbohydrates or cellulose derivatives. The carrier material, however, can also consist of a synthetic, biodegradable polymer. Those suitable are, inter alia, polyhydroxycarboxylic acids, polyesters, polycyanoacrylates, polyamino acids, polyalcohols and silicones. These carrier materials can preferably be employed as a web or as a fabric. Those particularly suitable are, for example, the commercially available web Ethisorb® Patch Type 6 from Ethicon and the collagen web Surgicoll from Medical Biomaterial Products. The web Ethisorb® Patch Type 6 from Ethicon is a synthetic, absorbable web made of polyglactin 910 (Vicryl®) and poly-p-dioxanone (PDS). Polyglactin 910 is a copolymer of glycolide and lactide. These webs or other degradable carrier materials can best be coated with the fibrin web during its production. In this case, a process is used such that the formation of the fibrin web takes place in the presence of the carrier material. To this end, the carrier material is introduced into the fibrinogen solution contained in a flat dish until it is completely covered with the liquid. A thrombin/calcium chloride solution is then sprayed on, as a result of which a fibrin web is formed which deposits on the carrier material and firmly adheres to it. In this process, a two-layer web of high flexibility is formed, which can be flexed without deformation of the coatings. The production of a multilayer wound covering of this type based on fibrin has the advantage of an improvement in the hemostatic effect in the case of heavily bleeding wounds. The flexibility of the carrier material is in this case not adversely affected by the fibrin web covering, as the fibrin web is very flexible when it has been prepared by the process according to the invention.

The fibrin web according to the invention can be further improved in its therapeutic value if biological, plant or synthetic active compounds such as immunoglobulins, chemotherapeutics or antibiotics which promote wound healing are added to it. It is expedient to add these substances to the fibrinogen solution beforehand in order that they are integrated into the fibrin web formed by the addition of thrombin. These substances, however, can also be applied to the finished fibrin web by spraying.

A remarkable improvement in the fibrin web according to the invention with respect to its tear resistance and elasticity can be achieved by addition of glycerol to the fibrinogen solution. If glycerol is added to the fibrinogen solution before fibrin formation in a percentage amount of between 0.2 and 1.0 percent by volume (v/v), a fibrin wound covering is obtained which contains 10 to 80% by weight of glycerol per fibrin unit, preferably 20 to 50 percent by weight of glycerol per fibrin unit. The tearing force and elasticity of the fibrin web thus modified by the addition of glycerol is so considerable that the fibrin web takes on a rubbery consistency. Moreover, the addition of glycerol has the advantage that it does not enter into any chemical reaction with the clotting factors. In contrast to this, in the case of wound coverings based on collagen an increase in the biomechanical stability can be achieved by means of chemical crosslinking, which, however, can have formation of potential neoantigens and thus poorer biocompatibility as a result.

The wound coverings according to the invention based on fibrin can be cut to the desired size, rolled up and unrolled again. In this way, they are also very readily employable in minimally invasive surgery.

The invention is illustrated in greater detail by the following examples:

EXAMPLE 1

Fibrinogen (Beriplast®) was taken up in water and dialyzed in 0.02 M sodium citrate. Dialysis in 0.05% NaCl was then carried out. The dialyzate was mixed with 15% glycerol and poured into previously provided metal troughs. A thrombin solution was subsequently sprayed onto the mixture and the mixture was then incubated at room temperature for 30 to 60 minutes. The resulting fibrin clot is frozen at −28° C. and freeze-dried in the following manner: the fibrin clot is first frozen at −28° C. for 12 hours and subsequently dried in vacuo at the same temperature for 12 hours. Two drying steps at −10° C. for 16 hours and at +25° C. for 8 hours then follow, a vacuum of $1.35 \times 10^{-1}$ mbar being applied.

EXAMPLE 2

Fibrinogen (Beriplast®) was taken up in water and dialyzed in 2 mM sodium citrate. Dialysis in 0.05% sodium chloride was subsequently carried out. The dialyzate was then processed further as in Example 1 and a flexible fibrin web was obtained after incubation with thrombin solution and subsequent freeze-drying.

EXAMPLE 3

Fibrinogen (Beriplast®) was taken up in water and dialyzed in 2 mM sodium citrate. Dialysis in 0.1% sodium chloride was subsequently carried out. After this, a flexible fibrin web was obtained by spraying on a thrombin solution, incubation for up to 60 minutes and subsequent freeze-drying.

EXAMPLE 4

Fibrinogen (Beriplast®) was taken up in water and dialyzed in a 2 mM sodium citrate solution. After this, a sufficient amount of a 10% strength sodium chloride solution was added until the fibrinogen solution contained 0.05% sodium chloride. The further production of the fibrin web was then carried out according to the above examples.

EXAMPLE 5

Fibrinogen (Beriplast®) was taken up in water and dialyzed in 2 mM sodium citrate and 0.05 to 0.07% sodium chloride. The fibrin web according to the invention was produced from this fibrinogen solution by addition of thrombin and subsequent freeze-drying as described in the above examples.

EXAMPLE 6

For production of the fibrin web, different amounts of glycerol in percent (v/v) were added to the fibrinogen solution before fibrin formation and the tensile strength and the elasticity of the web were subsequently measured in the dry and wet state. The results are shown in the following table:

TABLE

| Addition of glycerol in % | Tensile strength (N) | | Elasticity (mm) | |
|---|---|---|---|---|
| (v/v) | Dry web | Wet web | Dry web | Wet web |
| 0 | 1.5 | 0.6 | 3.6 | 28.1 |
| 0.2 | 2.0 | 0.5 | 11.8 | 33.9 |
| 0.4 | 1.8 | 1.1 | 16.1 | 36.4 |
| 0.8 | 2.3 | 1.5 | 25.7 | 48.7 |

The values in the table show that the addition of glycerol increases the mechanical stability and elasticity of the fibrin web in a concentration-dependent manner. These fibrin webs are suitable for use in surgery on internal organs and offer possibilities of use in endoscopy.

EXAMPLE 7

Fibrinogen (Beriplast®) was taken up in water and dialyzed in 2 mM sodium citrate. Dialysis in 0.07% NaCl was then carried out. The dialyzate was mixed with 15% glycerol. In a 5×5 cm metal trough, the web Ethisorb® Patch Type 6 (Ethicon GmbH) is adhered to the bottom of the trough, onto which was poured the dialyzate, and the formation of fibrin was induced by spraying on thrombin. After freeze-drying, a flexible, two-layer web resulted, in which both layers adhered well to one another.

What is claimed is:
1. A process for the production of a flexible wound covering based on fibrin, comprising:
   subjecting a fibrinogen solution to a single-stage or multistage dialysis,
   forming a flexible fibrin web by action of an aqueous thrombin solution on the fibrinogen solution, and
   freeze-drying the flexible fibrin web,
   wherein the fibrinogen solution is dialyzed in one stage with a solution containing a complexing agent and a physiologically compatible inorganic salt, and
   wherein the complexing agent is an aqueous solution of an alkali metal salt selected from the group consisting of ethylenediaminetetraacetic acid (EDTA), of oxalic acid or, of citric acid.
2. The process as claimed in claim 1, wherein the flexible fibrin web is largely or completely free of dialyzable constituents.
3. The process as claimed in claim 1, wherein the flexible fibrin web is firmly combined with a biodegradable support material.
4. The process as claimed in claim 3, wherein the flexible fibrin web contains from 10 to 80% by weight of glycerol per unit of fibrin.
5. The process as claimed in claim 1, wherein the flexible fibrin web contains from 10 to 80% by weight of glycerol per unit of fibrin.
6. The process as claimed in claim 1, wherein the formation of the flexible fibrin web is carried out in the presence of a biodegradable support material onto which the flexible fibrin web deposits as a firmly adhering layer.
7. The process as claimed in claim 6, wherein the biodegradable support material consists of natural or chemically modified collagen, keratin, gelatin, carbohydrates or cellulose derivatives.
8. The process as claimed in claim 6, wherein the biodegradable support material consists of a polymer from the group consisting of the polyhydroxycarboxylic acids, the polyesters, the polycyanoacrylates, the polyamino acids, the polyalcohols or the silicones.
9. The process as claimed in claim 1, wherein the fibrinogen solution additionally contains factor XIII.
10. The process as claimed in claim 1, wherein the concentration of the complexing agent in the dialysis bath is 1 to 20 mM.
11. The process as claimed in claim 10, wherein the concentration of the complexing agent in the dialysis bath is 1 to 5 mM.
12. The process as claimed in claim 1, wherein the physiologically compatible inorganic salt is present in the solution in an amount of up to 0.5 percent by weight.
13. The process as claimed in claim 1, wherein the physiologically compatible inorganic salt is NaCl.
14. The process as claimed in claim 1, wherein a water-soluble calcium salt is added to the aqueous thrombin solution.
15. The process as claimed in claim 14, wherein the water-soluble calcium salt is added in an amount from 0.5 to 40 mM.
16. The process as claimed in claim 1, wherein the fibrinogen solution is employed in an amount from 10 to 25 g/l and the thrombin is employed in an amount of less than 1000 I.U./ml.
17. The process as claimed in claim 1, wherein active compounds promoting wound healing are added to the flexible fibrin web.
18. The process as claimed in claim 1, wherein glycerol is added to the fibrinogen solution in an amount of 0.2 to 0.1 percent by volume during preparation of the flexible fibrin web.

* * * * *